(12) United States Patent
Kozai

(10) Patent No.: US 10,219,781 B2
(45) Date of Patent: Mar. 5, 2019

(54) ULTRASOUND OBSERVATION APPARATUS, METHOD FOR OPERATING ULTRASOUND OBSERVATION APPARATUS, AND COMPUTER-READABLE RECORDING MEDIUM

(71) Applicant: OLYMPUS CORPORATION, Tokyo (JP)

(72) Inventor: Shigenori Kozai, Tama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/422,504

(22) Filed: Feb. 2, 2017

(65) Prior Publication Data

US 2017/0143300 A1 May 25, 2017

Related U.S. Application Data

(63) Continuation of application No. PCT/JP2015/079967, filed on Oct. 23, 2015.

(30) Foreign Application Priority Data

Dec. 25, 2014 (JP) ................. 2014-262990

(51) Int. Cl.
  *A61B 8/00* (2006.01)
  *A61B 8/14* (2006.01)
  (Continued)

(52) U.S. Cl.
  CPC .............. *A61B 8/14* (2013.01); *A61B 5/7257* (2013.01); *A61B 8/5207* (2013.01); *A61B 8/5223* (2013.01); *A61B 8/5269* (2013.01)

(58) Field of Classification Search
  None
  See application file for complete search history.

(56) References Cited

U.S. PATENT DOCUMENTS

2013/0030296 A1* 1/2013 Miyaki ............... G01S 7/52033
  600/442
2013/0035594 A1 2/2013 Eda
  (Continued)

FOREIGN PATENT DOCUMENTS

JP  5568199 B1  8/2014
WO  WO 2012/063928 A1  5/2012

OTHER PUBLICATIONS

Japanese Office Action dated Apr. 8, 2016 received in Application No. 2016-509195.

(Continued)

*Primary Examiner* — Patricia J Park
(74) *Attorney, Agent, or Firm* — Scully, Scott, Murphy & Presser, P.C.

(57) ABSTRACT

Provided is an ultrasound observation apparatus for generating an ultrasound image based on an ultrasound signal acquired by an ultrasound probe having an ultrasound transducer. The apparatus includes: an analysis unit that performs FFT on a sample data group having pieces of sample data in RF data generated based on the ultrasound signal, to calculate frequency spectra; a correction unit that generates, based on the frequency spectra, analysis data indicating a relationship between a distance from the ultrasound transducer and an intensity of each of the frequency spectra for each frequency component, and corrects the analysis data based on a correction amount set for each distance, the correction amount causing an intensity of reference data generated from a reference ultrasound signal to be constant regardless of the distance; and a calculation unit that calculates a frequency feature based on a frequency spectrum generated in accordance with the corrected analysis data.

6 Claims, 8 Drawing Sheets

(51) Int. Cl.
*A61B 5/00* (2006.01)
*A61B 8/08* (2006.01)

(56) References Cited

U.S. PATENT DOCUMENTS

| | | |
|---|---|---|
| 2013/0113938 A1 | 5/2013 | Miyaki |
| 2013/0137982 A1* | 5/2013 | Lee ..................... A61B 8/5207 600/443 |
| 2014/0309531 A1 | 10/2014 | Eda |

OTHER PUBLICATIONS

International Search Report dated Jan. 19, 2016 issued in PCT/JP2015/079967.
Extended Supplementary European Search Report dated Aug. 14, 2018 in European Patent Application No. 15 87 2453.4.

* cited by examiner

ULTRASOUND OBSERVATION APPARATUS, METHOD FOR OPERATING ULTRASOUND OBSERVATION APPARATUS, AND COMPUTER-READABLE RECORDING MEDIUM

CROSS REFERENCES TO RELATED APPLICATIONS

This application is a continuation of PCT international application Ser. No. PCT/JP2015/079967, filed on Oct. 23, 2015 which designates the United States, incorporated herein by reference, and which claims the benefit of priority from Japanese Patent Application No. 2014-262990, filed on Dec. 25, 2014, incorporated herein by reference.

BACKGROUND

1. Technical Field

The disclosure relates to an ultrasound observation apparatus for observing tissues of an observation target by using ultrasound waves. The disclosure also relates to a method for operating the ultrasound observation apparatus, and to a computer-readable recording medium.

2. Related Art

Conventionally, as a technique for observing tissue characteristics of an observation target such as a specimen by using ultrasound waves, a technique that makes an image of a feature of a frequency spectrum of a received ultrasound signal has been known (for example, see JP 5568199 B1). In this technique, the feature of a frequency spectrum is extracted as an amount that represents the tissue characteristics of the observation target, and then a feature image obtained by adding corresponding visual information to the feature is generated and displayed. A user such as a doctor diagnoses the tissue characteristics of the specimen by seeing the displayed feature image.

For example, in JP 5568199 B1, the number of focus stages in an area set in an ultrasound image (hereinafter also referred to as an area of interest) and a plurality of focus positions are determined based on the position of the area of interest and the size of the area of interest, and the feature is calculated by performing frequency analysis on ultrasound waves transmitted to and received from each focus position.

SUMMARY

In some embodiments, provided is an ultrasound observation apparatus for generating an ultrasound image based on an ultrasound signal acquired by an ultrasound probe, the ultrasound probe having an ultrasound transducer configured to transmit an ultrasound wave to an observation target and to receive the ultrasound wave reflected from the observation target. The ultrasound observation apparatus includes: a frequency analysis unit configured to perform fast Fourier transform on a sample data group having a plurality of pieces of sample data in radio frequency data generated based on the ultrasound signal, thereby to calculate a plurality of frequency spectra; an analysis data correction unit configured to: generate, based on the plurality of frequency spectra calculated by the frequency analysis unit, analysis data indicating a relationship between a distance from the ultrasound transducer and an intensity of each of the frequency spectra for each frequency component; and correct the analysis data based on a correction amount set for each distance, the correction amount causing an intensity of reference data generated from a reference ultrasound signal to be constant regardless of the distance; a feature calculation unit configured to calculate a frequency feature based on a frequency spectrum generated in accordance with the analysis data corrected by the analysis data correction unit; and a feature image data generation unit configured to generate feature image data for displaying the frequency feature calculated by the feature calculation unit along with the ultrasound image, in association with visual information.

In some embodiments, provided is a method for operating an ultrasound observation apparatus, the ultrasound observation apparatus being configured to generate an ultrasound image based on an ultrasound signal acquired by an ultrasound probe, the ultrasound probe having an ultrasound transducer configured to transmit an ultrasound wave to an observation target and to receive the ultrasound wave reflected from the observation target. The method includes: performing, by a frequency analysis unit, fast Fourier transform on a sample data group having a plurality of pieces of sample data on radio frequency data generated based on the ultrasound signal, thereby to calculate a plurality of frequency spectra; generating, by an analysis data correction unit, based on the plurality of frequency spectra calculated by the frequency analysis unit, analysis data indicating a relationship between a distance from the ultrasound transducer and an intensity of each of the frequency spectra for each frequency component, and correcting the analysis data based on a correction amount set for each distance, the correction amount causing an intensity of reference data generated from a reference ultrasound signal to be constant regardless of the distance; calculating, by a feature calculation unit, a frequency feature based on a frequency spectrum generated in accordance with the analysis data corrected by the analysis data correction unit; and generating, by a feature image data generation unit, feature image data for displaying the frequency feature calculated by the feature calculation unit along with the ultrasound image, in association with visual information.

In some embodiments, provided is a non-transitory computer-readable recording medium with an executable program stored thereon for operating an ultrasound observation apparatus, the ultrasound observation apparatus being configured to generate an ultrasound image based on an ultrasound signal acquired by an ultrasound probe, the ultrasound probe having an ultrasound transducer configured to transmit an ultrasound wave to an observation target and to receive the ultrasound wave reflected from the observation target. The program causes the ultrasound observation apparatus to execute: performing, by a frequency analysis unit, fast Fourier transform on a sample data group having a plurality of pieces of sample data on radio frequency data generated based on the ultrasound signal, thereby to calculate a plurality of frequency spectra; generating, by an analysis data correction unit, based on the plurality of frequency spectra calculated by the frequency analysis unit, analysis data indicating a relationship between a distance from the ultrasound transducer and an intensity of each of the frequency spectra for each frequency component, and correcting the analysis data based on a correction amount set for each distance, the correction amount causing an intensity of reference data generated from a reference ultrasound signal to be constant regardless of the distance; calculating, by a feature calculation unit, a frequency feature based on a frequency spectrum generated in accordance with the analysis data corrected by the analysis data correction unit; and generating, by a feature image data generation unit, feature image data for displaying the frequency feature calculated by the feature calculation unit along with the ultrasound image, in association with visual information.

The above and other features, advantages and technical and industrial significance of this invention will be better understood by reading the following detailed description of presently preferred embodiments of the invention, when considered in connection with the accompanying drawings.

DETAILED DESCRIPTION

Hereinafter, modes for carrying out the invention (hereinafter referred to as "embodiment(s)") will be described with reference to the drawings.

Embodiments

Figure 1:
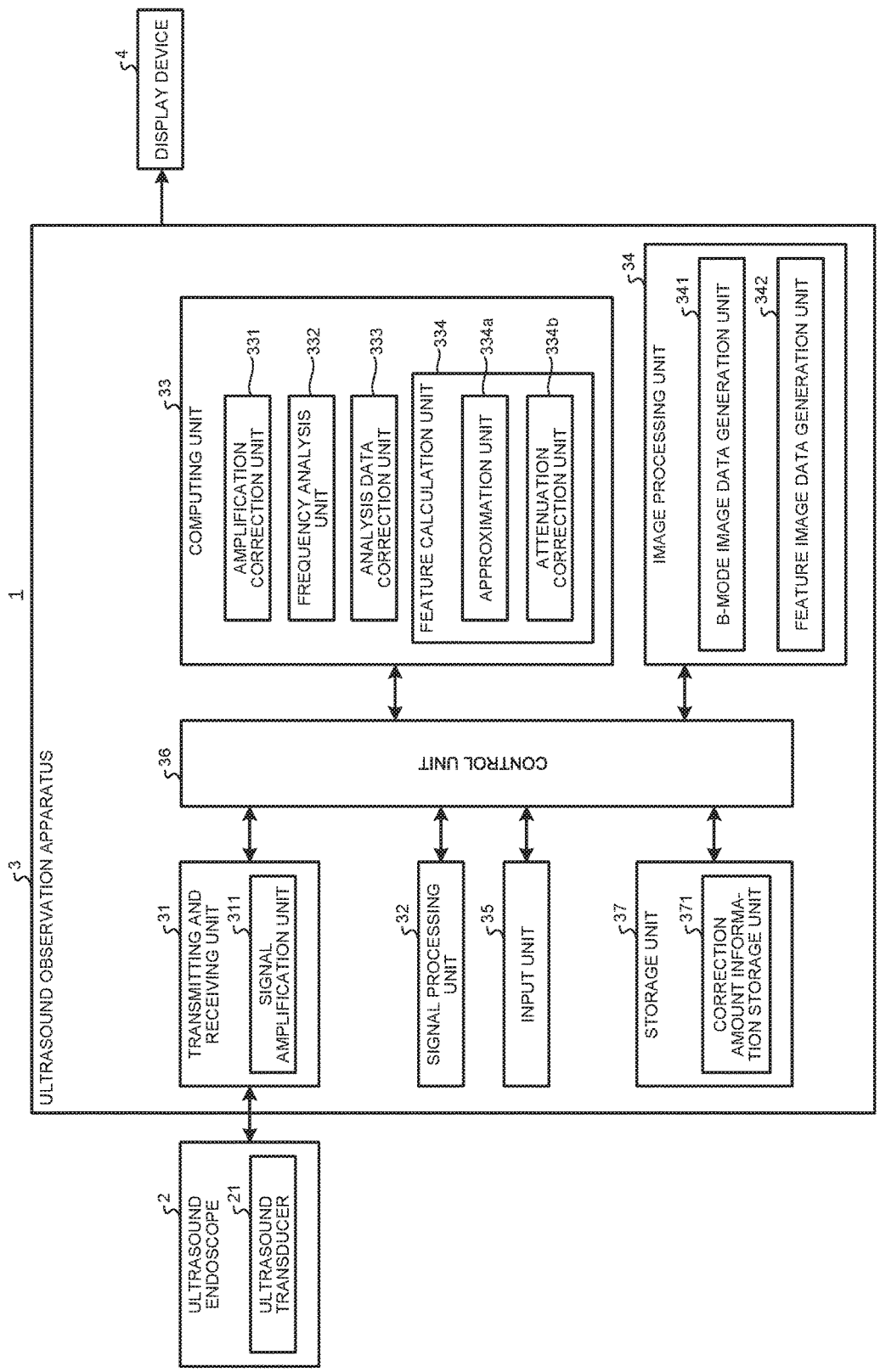
FIG. 1 is a block diagram illustrating a configuration of an ultrasound diagnosis system having an ultrasound observation apparatus according to an embodiment of the present invention.

FIG. 1 is a block diagram illustrating a configuration of an ultrasound diagnosis system 1 having an ultrasound observation apparatus 3 according to an embodiment of the present invention. The ultrasound diagnosis system 1 illustrated in FIG. 1 includes an ultrasound endoscope 2 (ultrasound probe) configured to transmit ultrasound waves to a subject as an observation target and to receive the ultrasound waves reflected from the subject, the ultrasound observation apparatus 3 configured to generate an ultrasound image based on an ultrasound signal acquired by the ultrasound endoscope 2, and a display device 4 configured to display the ultrasound image generated by the ultrasound observation apparatus 3.

The ultrasound endoscope 2 includes an ultrasound transducer 21, which converts an electrical pulse signal received from the ultrasound observation apparatus 3 into an ultrasound pulse (acoustic pulse) and emits the ultrasound pulse to the subject and which converts an ultrasound echo reflected from the subject into an electrical echo signal that represents the ultrasound echo as a voltage variation and outputs the echo signal, at the distal end portion of the ultrasound endoscope 2. The ultrasound transducer 21 may be any one of a convex transducer, a linear transducer, and a radial transducer. The ultrasound endoscope 2 may be an endoscope that causes the ultrasound transducer 21 to mechanically scan or an endoscope that causes the ultrasound transducer 21 to electronically scan by providing a plurality of elements in an array shape as the ultrasound transducer 21 and electronically switching elements related to transmission and reception and/or delaying transmission and reception of each element.

The ultrasound endoscope 2 normally includes an imaging optical system and an image sensor. The ultrasound endoscope 2 is inserted into a digestive tract (esophagus, stomach, intestine duodenum, or large intestine) or a respiratory organ (windpipe or bronchus) of the subject and can capture an image of the digestive tract, the respiratory organ, or their surrounding organ (pancreas, gall bladder, bile duct, biliary tract, lymph node, mediastinal organ, blood vessel, or the like). The ultrasound endoscope 2 also includes a light guide that guides illumination light emitted to the subject while capturing an image. The distal end portion of the light guide reaches the distal end of an insertion portion of the subject of the ultrasound endoscope 2. On the other hand, the proximal end portion of the light guide is connected to a light source apparatus that generates the illumination light. The ultrasound observation system 1 is not limited to include the ultrasound endoscope 2, but may include an ultrasound probe that does not have an imaging optical system and an image sensor.

The ultrasound observation apparatus 3 includes a transmitting and receiving unit 31 that is electrically connected to the ultrasound endoscope 2, transmits a transmission signal (a pulse signal) formed of a high-voltage pulse based on a predetermined waveform and a transmission timing to the ultrasound transducer 21, and generates and outputs data (hereinafter referred to as RF data) of a digital high frequency (RF: Radio Frequency) signal by receiving an echo signal that is an electrical reception signal from the ultrasound transducer 21, a signal processing unit 32 that generates digital B-mode reception data based on the RF data received from the transmitting and receiving unit 31, a computing unit 33 that performs a predetermined calculation on the RF data received from the transmitting and receiving unit 31, an image processing unit 34 that generates various image data, an input unit 35 that is realized by using a user interface such as a keyboard, a mouse, and a touch panel and receives input of various information, a control unit 36 that controls the entire ultrasound observation system 1, and a storage unit 37 that stores various information necessary for operation of the ultrasound observation apparatus 3.

Figure 2:
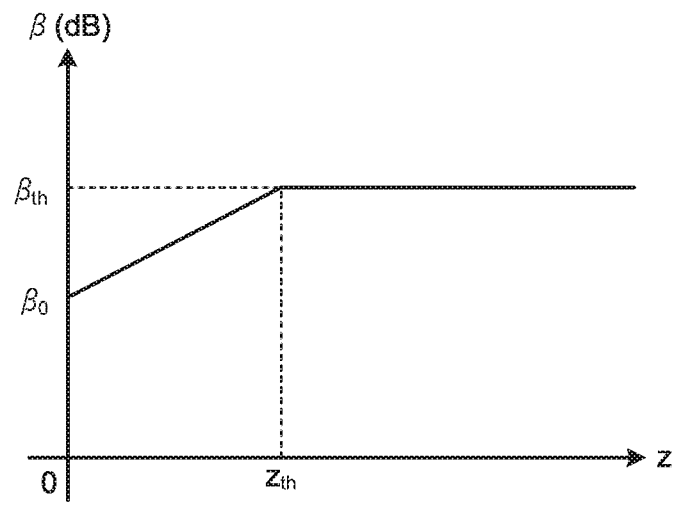
FIG. 2 is a graph illustrating a relationship between a reception depth and an amplification factor in amplification processing performed by a signal amplification unit of the ultrasound observation apparatus according to the embodiment of the present invention.

The transmitting and receiving unit 31 includes a signal amplification unit 311 that amplifies the echo signal. The signal amplification unit 311 performs STC (Sensitivity Time Control) correction in which the greater a reception depth of the echo signal, the higher an amplification factor by which the echo signal is amplified. FIG. 2 is a graph illustrating a relationship between the reception depth and the amplification factor in amplification processing performed by the signal amplification unit 311. A reception depth z illustrated in FIG. 2 is an amount calculated based on an elapsed time from a time point when reception of an ultrasound wave is started. As illustrated in FIG. 2, when the reception depth z is smaller than a threshold value $z_{th}$, an amplification factor β (dB) linearly increases from $β_0$ to $β_{th}$ ($>β_0$) along with increase of the reception depth z. When the reception depth z is equal to or greater than the threshold value $z_{th}$, the amplification factor β (dB) is a constant value $β_{th}$. The threshold value $z_{th}$ is a value where the ultrasound signal received from the observation target attenuates too much and noise becomes dominant. More generally, when the reception depth z is smaller than the threshold value $z_{th}$, the amplification factor β should monotonically increase along with increase of the reception depth z. The relationship illustrated in FIG. 2 is stored in the storage unit 37 in advance.

The transmitting and receiving unit 31 performs processing such as filtering and the like on the echo signal amplified by the signal amplification unit 311 and then generates time-domain RF data by A/D converting the echo signal and outputs the RF data to the signal processing unit 32 and the computing unit 33. When the ultrasound endoscope 2 has a configuration in which the ultrasound transducer 21 where a plurality of elements are provided in an array shape is electrically scanned, the transmitting and receiving unit 31 has a multi-channel circuit for synthesizing a beam corresponding to the plurality of elements.

It is recommended that a frequency band of the pulse signal transmitted by the transmitting and receiving unit 31 is a wide band that substantially covers a linear response frequency band of electroacoustic conversion of the pulse signal into an ultrasound pulse in the ultrasound transducer 21. It is also recommended that various processing frequency bands of the echo signal in the signal amplification unit 311 are wide bands that substantially cover a linear response frequency band of electroacoustic conversion of the ultrasound echo into the echo signal by the ultrasound transducer 21. Thus, it is possible to perform accurate approximation when performing approximate processing of a frequency spectrum described later.

The transmitting and receiving unit 31 has also a function to transmit various control signals outputted by the control unit 36 to the ultrasound endoscope 2 and a function to receive various information including an identification ID from the ultrasound endoscope 2 and transmit the various information to the control unit 36.

The signal processing unit 32 performs known processing such as bandpass filter, envelope detection, and logarithmic conversion on the RF data and generates digital B-mode reception data. In the logarithmic conversion, a common logarithm of a value obtained by dividing the RF data by a reference voltage $V_c$ is represented as a decibel value. The signal processing unit 32 outputs the generated B-mode reception data to the image processing unit 34. The signal processing unit 32 is realized by using a CPU (Central Processing Unit), various calculation circuits, and the like.

The computing unit 33 includes an amplification correction unit 331 that performs amplification correction on the RF data generated by the transmitting and receiving unit 31 so that the amplification factor β is constant regardless of the reception depth, a frequency analysis unit 332 that calculates a frequency spectrum by performing frequency analysis by performing Fast Fourier Transform (FFT) on the RF data on which the amplification correction is performed, an analysis data correction unit 333 that corrects analysis data, which is a distance (reception depth) spectrum generated for each frequency component, based on the frequency spectrum calculated by the frequency analysis unit 332, and a feature calculation unit 334 that calculates a feature of the frequency spectrum. The computing unit 33 is realized by using a CPU (Central Processing Unit), various calculation circuits, and the like.

Figure 3:
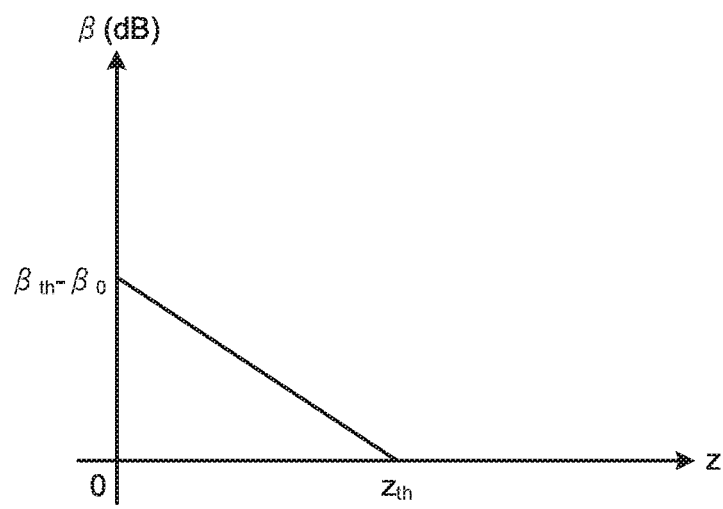
FIG. 3 is a graph illustrating a relationship between a reception depth and an amplification factor in amplification correction processing performed by an amplification correction unit of the ultrasound observation apparatus according to the embodiment of the present invention.

FIG. 3 is a graph illustrating a relationship between the reception depth and the amplification factor in the amplification correction processing performed by the amplification correction unit 331. As illustrated in FIG. 3, an amplification factor β (dB) in the amplification correction processing performed by the amplification correction unit 331 takes a maximum value $β_{th}−β_0$ when the reception depth z is zero, linearly decreases while the reception depth z changes from zero to the threshold value $z_{th}$, and takes zero when the reception depth z is equal to or greater than the threshold value $z_{th}$. The amplification correction unit 331 performs the amplification correction on the digital RF signal using the amplification factor determined in this way, thereby to offset an effect of the STC correction in the signal processing unit 32 and to output a signal of a constant amplification factor $β_{th}$. Of course, the relationship between the reception depth z and the amplification factor β in the amplification correction processing performed by the amplification correction unit 331 differs depending on the relationship between the reception depth and the amplification factor in the signal processing unit 32.

The reason for performing such amplification correction will be described. The STC correction is correction processing that eliminates effects of attenuation from an amplitude of an analog signal waveform by amplifying the amplitude of the analog signal waveform by an amplification factor which is uniform over all frequency bands and monotonically increases with respect to the depth. Therefore, when a B-mode image that is displayed by converting the amplitude of echo signal into luminance is generated and when homogeneous tissues are scanned, a luminance value becomes constant regardless of the depth by performing the STC correction. That is to say, it is possible to obtain an effect of eliminating the effects of attenuation from the luminance value of the B-mode image.

On the other hand, as in the embodiment, when a result of analysis of calculation of the frequency spectrum of ultrasound wave is used, even the STC correction cannot correctly eliminate the effect of attenuation accompanying propagation of the ultrasound wave. Because, although the amount of attenuation generally varies according to frequency (see formula (1) described later), the amplification factor of the STC correction varies according to distance only and does not have frequency dependency.

To solve the above problem, that is, the problem where when using the result of analysis of calculation of the frequency spectrum of ultrasound wave, even the STC correction cannot correctly eliminate the effect of attenuation accompanying propagation of the ultrasound wave, it is considered to output a reception signal on which the STC correction is performed when generating the B-mode image and further to perform new transmission different from transmission to generate the B-mode image and output a reception signal on which the STC correction is not performed when generating an image based on the frequency spectrum. However, in this case, there is a problem that a frame rate of image data generated based on the reception signal decreases.

Therefore, in the embodiment, the amplification factor is corrected by the amplification correction unit 331 in order to eliminate effects of the STC correction from the signal on which the STC correction is performed for the B-mode image while maintaining the frame rate of image data to be generated.

The frequency analysis unit 332 samples RF data (line data) of each sound ray, on which amplification correction is performed by the amplification correction unit 331, at a predetermined time intervals and generates sample data. The frequency analysis unit 332 calculates a frequency spectrum at a plurality of positions (data positions) on the RF data by performing FFT processing on a sample data group. The "frequency spectrum" mentioned here means a "frequency distribution of intensity at a certain reception depth z" obtained by performing FFT processing on a sample data group. The "intensity" mentioned here indicates, for example, any one of parameters such as a voltage of echo signal, an electric power of echo signal, a sound pressure of ultrasound echo, and an acoustic energy of ultrasound echo, amplitudes and time integration values of these parameters, and a combination of these.

In general, when the observation target is a living tissue, the frequency spectrum shows different tendency depending on characteristics of the living tissue that is scanned by an ultrasound wave. This is because the frequency spectrum has correlation with the size, the number density, the acoustic impedance, and the like of a scattering body that scatters ultrasound waves. The "characteristics of the living tissue" mentioned here are, for example, malignant tumor (cancer), benign tumor, endocrine tumor, mucinous tumor, normal tissue, cyst, vascular channel, and the like.

Figure 4:
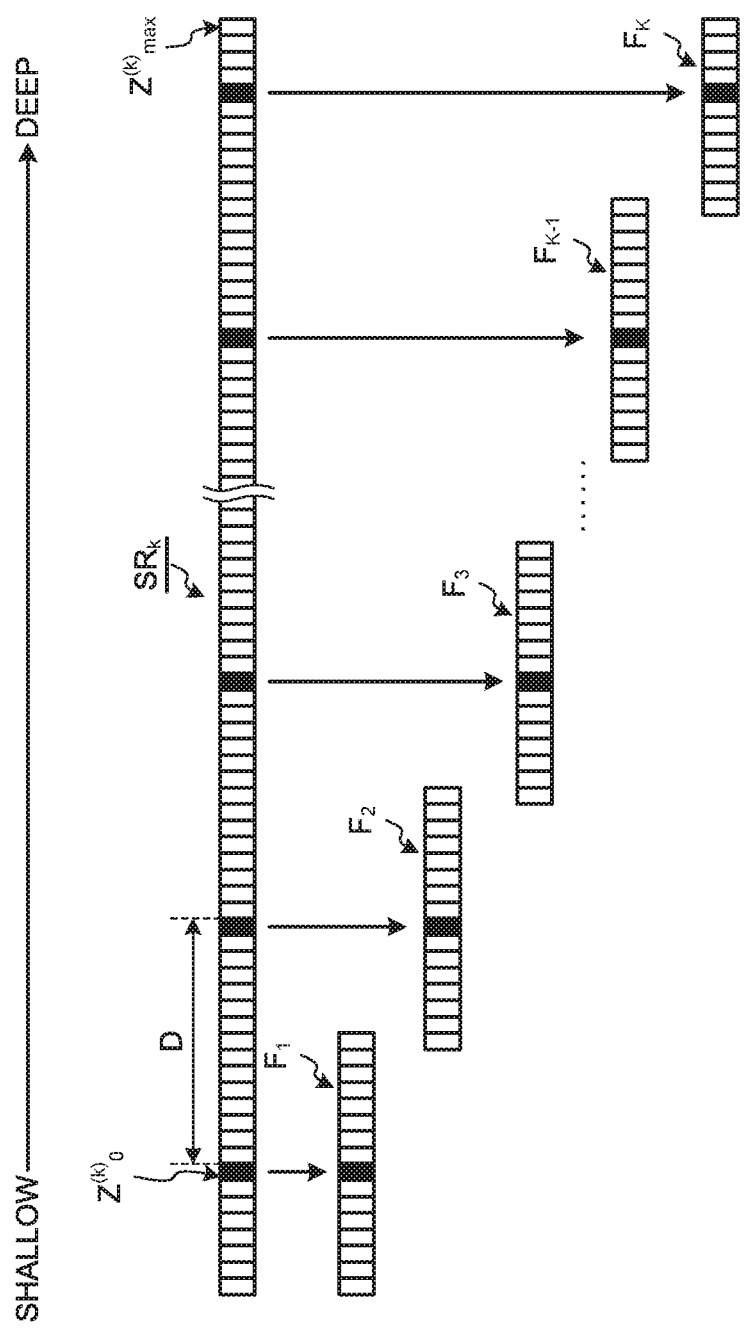
FIG. 4 is a diagram schematically illustrating a data arrangement in one sound ray of an ultrasound signal.

FIG. 4 is a diagram schematically illustrating a data arrangement in one sound ray of an ultrasound signal. In a sound ray $SR_k$ illustrated in FIG. 4, a white or black rectangle means data at one sample point. Further, on the sound ray $SR_k$, the more right the data is positioned, the deeper the position from which the data, which is sample data, is obtained when measured along the sound ray $SR_k$ from the ultrasound transducer 21 (see an arrow in FIG. 4). The sound ray $SR_k$ is discretized at time intervals corresponding to a sampling frequency (for example, 50 MHz) in A/D conversion performed by the transmitting and receiving unit 31. FIG. 4 illustrates a case in which an eighth data position of the sound ray $SR_k$ of a number k is set as an initial value $Z^{(k)}_0$ in a direction of the reception depth z. However, the position of the initial value can be arbitrarily set. A calculation result of the frequency analysis unit 332 is obtained as a complex number and stored in the storage unit 37.

A data group $F_j$ (j=1, 2, . . . , and K) illustrated in FIG. 4 is a sample data group to be a target of the FFT processing. In general, to perform the FFT processing, the sample data group should have the number of data of power-of-two. Thus, the number of data of the sample data group $F_j$ (j=1, 2, . . . , and K−1) is 16 (=$2^4$), so that the sample data group $F_j$ is a normal data group. On the other hand, the number of data of the sample data group $F_K$ is 12, so that the sample data group $F_K$ is an abnormal data group. When performing the FFT processing on an abnormal data group, processing is performed that generates a normal sample data group by inserting zero data to fill in the gaps. This will be described in detail when the processing of the frequency analysis unit 332 is described (see FIG. 9).

The analysis data correction unit 333 generates analysis data indicating a relationship between a signal value (intensity of a frequency spectrum) and a distance (a reception depth) for each reception depth of a certain frequency based on a plurality of frequency spectra calculated by the frequency analysis unit 332 and corrects the analysis data based on a correction amount for each reception depth that is set in advance.

Figure 5:
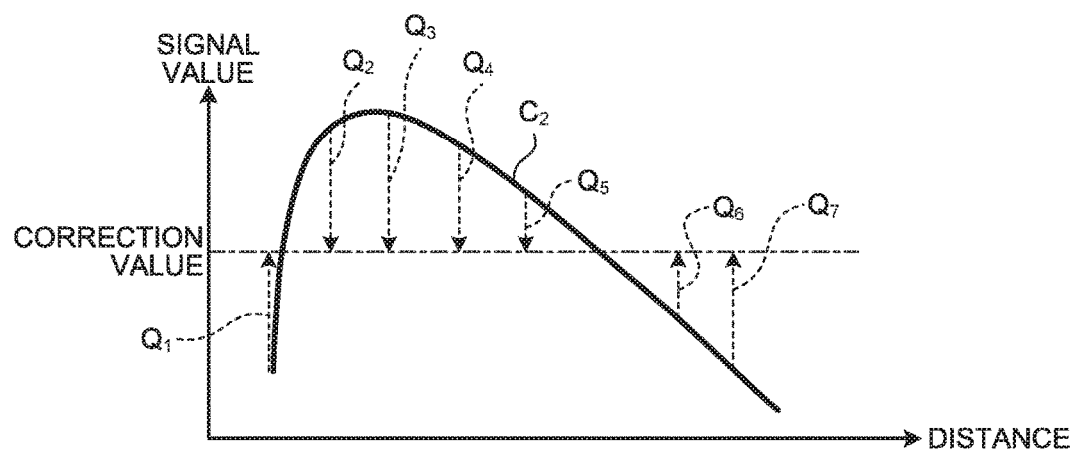
FIG. 5 is a graph illustrating an example of reference data for calculating a correction amount used for correction processing performed by an analysis data correction unit of the ultrasound observation apparatus according to the embodiment of the present invention.

FIG. 5 is a graph illustrating an example of reference data for calculating a correction amount used for correction processing performed by the analysis data correction unit 333. The reference data indicates a relationship between a distance (reception depth) from the ultrasound transducer 21 at certain frequency component and focus position and a signal value (intensity of the signal). In FIG. 5, the horizontal axis represents the distance (reception depth) from the ultrasound transducer 21. Regarding the reference data, an ultrasound wave is transmitted to an object for scattering the ultrasound wave uniformly or to a strong reflector so as to obtain a predetermined focus position and a predetermined frequency, and the reference data is calculated based on the intensity of the obtained signal (reference ultrasound signal). Here, the object that scatters the ultrasound wave uniformly is an object that reflects the ultrasound wave while transmitting the ultrasound wave according to the frequency. The object is formed of a material that shows scattering characteristics similar to those of a living organism and is generally referred to as a living organism simulative phantom. The strong reflector is an object where reflection of the ultrasound wave is more dominant than scattering of the ultrasound wave. The strong reflector is formed of a material such as a metal whose acoustic impedance is significantly different from that of a living organism.

In FIG. 5, the vertical axis represents a signal value of a reception depth at a certain frequency. For example, when the frequency is 5 MHz, a curved line $C_2$ as illustrated in FIG. 5 is acquired for each focus position that can be set (for example, 1 mm, 2 mm, 3 mm, and so on). When there is a plurality of frequencies outputted by the transducer, the reference data is generated for each frequency. For example, when the frequency can be set to 5 MHz, 10 MHz, and 25 MHz and the focus position can be set to 1 mm, 2 mm, and 3 mm for each frequency, nine reference data can be obtained. The embodiment is described by using a long-distance sound wave as an example. The same goes for a short-distance radio wave.

The correction amount is a difference between the reference data (signal value) set for each reception depth and a correction value (for example, differences $Q_1$ to $Q_7$ illustrated in FIG. 5). The correction value is a value that is set for each frequency component and each focus position or for each type of the ultrasound endoscope 2. The correction value is a constant value regardless of a distance, and for example, is set based on a ratio to a peak of a signal value in an apparatus setting, characteristics of the transducer, and the like. In other words, the correction amount is an amount (value) that causes the signal value of the reference data in the frequency component to be constant regardless of a distance (reception depth). The correction amount is stored in a correction amount information storage unit 371 described later for each frequency component and for each focus position.

The analysis data correction unit 333 corrects the signal value of each reception depth based on the generated analysis data. Specifically, the analysis data correction unit 333 corrects the signal value in the frequency component by adding or subtracting the correction amount described above to or from the signal value of each reception depth based on the analysis data.

The analysis data correction unit 333 corrects the signal value of each reception depth and then restores the signal value to a frequency spectrum as a frequency distribution of intensity at a certain reception depth z, that is, a frequency spectrum calculated by the frequency analysis unit 332, based on the analysis data after the correction, and outputs the frequency spectrum to the feature calculation unit 334.

Figure 6:
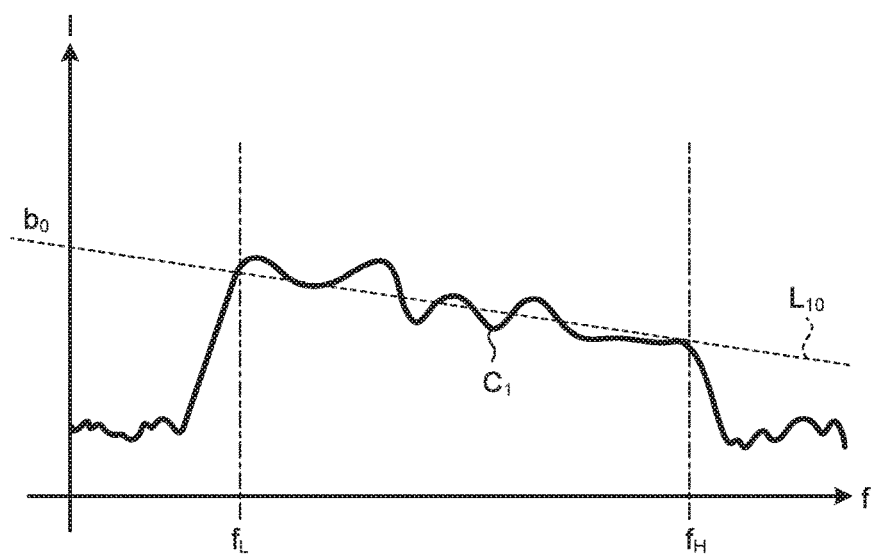
FIG. 6 is a graph illustrating an example of a frequency spectrum after correction by the analysis data correction unit of the ultrasound observation apparatus according to the embodiment of the present invention.

FIG. 6 is a graph illustrating an example of the frequency spectrum that has been corrected by the analysis data correction unit 333. In FIG. 6, the horizontal axis represents a frequency f. In FIG. 6, the vertical axis represents a common logarithm (decibel) $I=10\log_{10}(I_0/I_c)$ that is an amount obtained by dividing an intensity $I_0$ by a reference intensity $I_c$ (constant). A straight line $L_{10}$ illustrated in FIG. 6 will be described later. In the embodiment, a curved line and a straight line are formed from a set of discrete points.

In a frequency spectrum $C_1$ illustrated in FIG. 6, a lower limit frequency $f_L$ and an upper limit frequency $f_H$ of a frequency band used in calculations thereafter are parameters determined based on the frequency band of the ultrasound transducer 21, the frequency band of the pulse signal transmitted by the transmitting and receiving unit 31, and the like. Hereinafter, the frequency band determined by the lower limit frequency $f_L$ and the upper limit frequency $f_H$ in FIG. 6 is referred to as "frequency band F".

The feature calculation unit 334 calculates a feature of each of a plurality of frequency spectra outputted from the analysis data correction unit 333. The feature calculation unit 334 includes an approximation unit 334a that calculates a feature (hereinafter referred to as a pre-correction feature) of the frequency spectrum before performing attenuation correction processing by approximating the frequency spectrum by a straight line and an attenuation correction unit 334b that calculates a feature by performing attenuation correction on the pre-correction feature calculated by the approximation unit 334a.

The approximation unit 334a approximates the frequency spectrum by a linear expression (regression line) by performing regression analysis of the frequency spectrum in a predetermined frequency band and thereby calculates the pre-correction feature that features the approximated linear expression. For example, in the case of the frequency spectrum $C_1$ illustrated in FIG. 6, (in the case of a frequency spectrum that has been corrected by the analysis data correction unit 333), the approximation unit 334a obtains a regression line $L_{10}$ by performing regression analysis in a frequency band F and approximating the frequency spectrum $C_1$ by a linear expression. In other words, the approximation unit 334a calculates a slope $a_0$ of the regression line $L_{10}$, an intercept $b_0$, and a Mid-band fit $c_0=a_0f_M+b_0$ which is a value on a regression line of a center frequency $f_M=(f_L+f_H)/2$ of the frequency band F as the pre-correction feature.

Among the three pre-correction feature, the slope $a_0$ is correlated with the size of a scattering body of an ultrasound wave, and in general, it is considered that the greater the scattering body, the smaller the value of the slope. The intercept $b_0$ is correlated with the size of a scattering body, a difference of acoustic impedance, a number density (density) of scattering bodies, and the like. Specifically, it is considered that the larger the scattering body, the greater the value of the intercept $b_0$ is, the larger the difference of acoustic impedance, the greater the value of the intercept $b_0$ is, and the larger the number density of scattering bodies, the greater the value of the intercept $b_0$ is. The Mid-band fit $c_0$ is an indirect parameter derived from the slope $a_0$ and the intercept $b_0$ and provides an intensity of a spectrum at the center of an effective frequency band. Therefore, it is considered that the Mid-band fit $c_0$ is somewhat correlated with the luminance of a B-mode image in addition to the size of a scattering body, the difference of acoustic impedance, and the number density of scattering bodies. The feature calculation unit 334 may approximate a frequency spectrum by a second or higher order polynomial using regression analysis.

The correction performed by the attenuation correction unit 334b will be described. In general, an attenuation amount A(f, z) of an ultrasound wave is attenuation generated while the ultrasound wave reciprocates between reception depth 0 and reception depth z and is defined as intensity change (difference in decibels) before and after the reciprocation. It is empirically known that the attenuation amount A(f, z) is proportional to frequency in a uniform tissue and the attenuation amount A(f, z) is represented by the following formula (1).

$$A(f,z)=2\alpha z f \quad (1)$$

Here, the proportional constant α is an amount called an attenuation rate. Further, z is the reception depth of the ultrasound wave and f is the frequency. When the observation target is a living organism, a specific value of the attenuation rate α is determined according to a region of the living organism. The unit of the attenuation rate α is, for example, dB/cm/MHz. In the embodiment, it is also possible to change the value of the attenuation rate α by an input from the input unit 35.

The attenuation correction unit 334b calculates features a, b, and c by performing attenuation correction according to the formulas (2) to (4) shown below on the pre-correction features (slope $a_0$, intercept $b_0$, and Mid-band fit $c_0$) extracted by the approximation unit 334a.

$$a=a_0+2\alpha z \quad (2)$$

$$b=b_0 \quad (3)$$

$$c=c_0+A(f_M,z)=c_0+2\alpha z f_M(=af_M+b) \quad (4)$$

As is clear from the formulas (2) and (4), the larger the reception depth z of the ultrasound wave, the larger the correction amount of correction performed by the attenuation correction unit 334b. According to the formula (3), correction related to the intercept is identity transformation. This is because the intercept is a frequency component corresponding to frequency 0 (Hz) and is not affected by attenuation.

Figure 7:
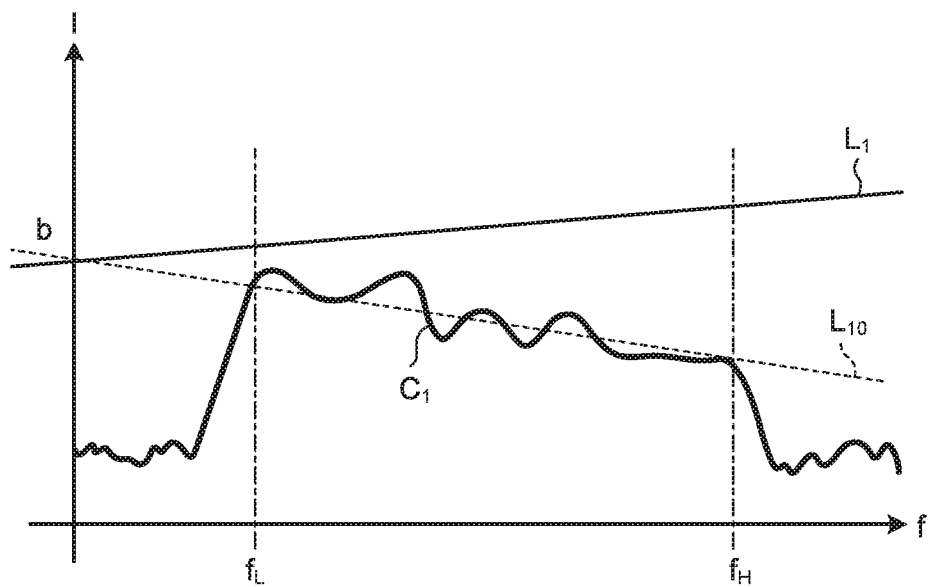
FIG. 7 is a graph illustrating a straight line which includes a correction feature corrected by an attenuation correction unit of the ultrasound observation apparatus according to the embodiment of the present invention as a parameter.

FIG. 7 is a graph illustrating a straight line including the features a, b, and c, which are calculated by the attenuation correction unit 334b, as parameters. A formula of a straight line $L_1$ is represented as follows:

$$I=af+b=(a_0+2\alpha z)f+b_0 \quad (5)$$

As is clear from the formula (5), regarding the straight line $L_1$, the slope is large ($a>a_0$) and the intercept is the same ($b=b_0$) as compared with the straight line $L_{10}$ before the attenuation correction.

The image processing unit 34 includes a B-mode image data generation unit 341 that generates B-mode image data which is an ultrasound image that is displayed by converting the amplitude of echo signal into luminance and a feature image data generation unit 342 that generates feature image data for displaying the feature calculated by the attenuation correction unit 334b along with the B-mode image in association with visual information.

The B-mode image data generation unit 341 generates the B-mode image data by performing signal processing using known techniques such as gain processing and contrast processing on the B-mode reception data received from the signal processing unit 32 and performing data thinning according to a data step width determined according to a display range of an image in the display device 4. The B-mode image is a grayscale image in which the values of R (red), G (green), and B (blue), which are variables when employing an RGB colorimetric system as a color space, are caused to be the same.

The B-mode image data generation unit 341 generates the B-mode image data by performing coordinate conversion, in which the B-mode reception data received from the signal processing unit 32 is rearranged so that a scanning range can be spatially correctly represented, on the B-mode reception data and thereafter filling gaps between the B-mode reception data by performing interpolation processing between the B-mode reception data. The B-mode image data generation unit 341 outputs the generated B-mode image data to the feature image data generation unit 342.

The feature image data generation unit 342 generates the feature image data by superimposing the visual information related to the feature calculated by the feature calculation unit 334 on each pixel of the image in the B-mode image data. For example, the feature image data generation unit 342 assigns visual information corresponding to a feature of a frequency spectrum calculated from one sample data group $F_j$ (j=1, 2, . . . , K) illustrated in FIG. 4 on a pixel area corresponding to a data amount of the sample data group $F_j$. The feature image data generation unit 342 generates a feature image by, for example, associating a color phase as visual information with any one of the slope, the intercept, and the Mid-band fit described above. The feature image data generation unit 342 may generates the feature image data by associating a color phase with any one of two features selected from the slope, the intercept, and the Mid-band fit and associating brightness with the other feature. Examples of the visual information related to the feature include variables of a color space that forms a predetermined color system, such as color phase, chroma, brightness, luminance value, R (red), G (green), and B (blue).

The control unit 36 is realized by using a CPU (Central Processing Unit) that has calculation and control functions, various calculation circuits, and the like. The control unit 36 integrally controls the ultrasound observation apparatus 3 by reading information stored in the storage unit 37 from the storage unit 37 and performing various calculation processing related to an operation method of the ultrasound observation apparatus 3. The control unit 36 may share the same CPU with the signal processing unit 32 and the computing unit 33.

The storage unit 37 stores a plurality of features calculated by the attenuation correction unit 334b for each frequency spectrum and image data generated by the image processing unit 34. The storage unit 37 includes the correction amount information storage unit 371 that stores the correction amount described above for each frequency component and for each focus position.

Other than the above, the storage unit 37 also stores, for example, information necessary for the amplification processing (the relationship between the amplification factor and the reception depth illustrated in FIG. 2), information necessary for the amplification correction processing (the relationship between the amplification factor and he reception depth illustrated in FIG. 3), information necessary for the attenuation correction processing (see the formula (1)), and information of window functions (such as Hamming, Hanning, and Blackman) necessary for frequency analysis processing.

Further, the storage unit 37 stores various programs including an operation program for performing the operation method of the ultrasound observation apparatus 3. The operation program can be recorded in a recording medium such as a hard disk, a flash memory, a CD-ROM, a DVD-ROM, and a flexible disk that can be read by a computer and can be widely distributed. It is possible to acquire the various programs mentioned above by downloading the programs through a communication network. The communication network mentioned here is realized by, for example, an existing public network, a LAN (Local Area Network), and a WAN (Wide Area Network) regardless of wired or wireless.

The storage unit 37 having the configuration described above is realized by using a ROM (Read Only Memory) in which various programs and the like are installed in advance, a RAM (Random Access Memory) that stores calculation parameters and data for each processing, and the like.

Figure 8:
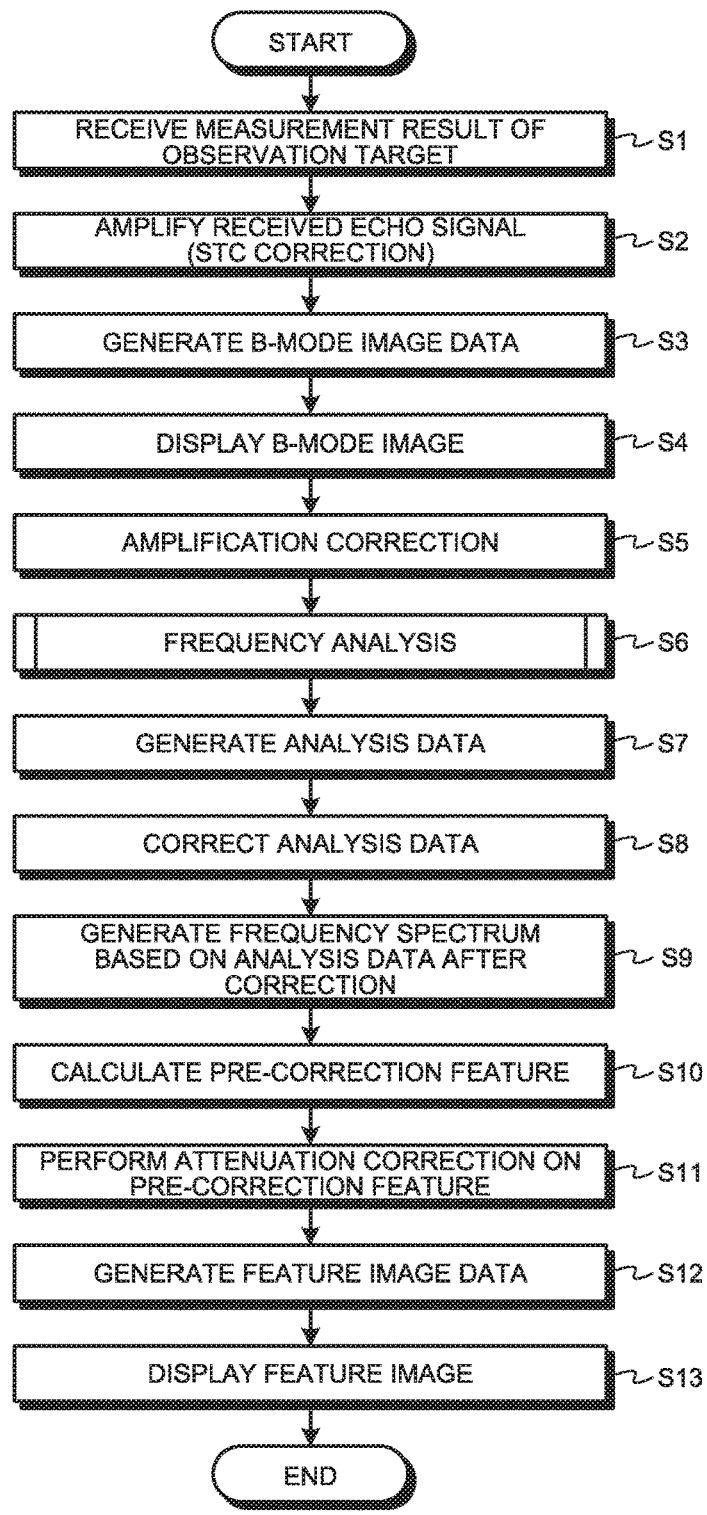
FIG. 8 is a flowchart illustrating an overview of processing performed by the ultrasound observation apparatus according to the embodiment of the present invention.

FIG. 8 is a flowchart illustrating an overview of processing performed by the ultrasound observation apparatus 3 having the configuration described above. First, the ultrasound observation apparatus 3 receives an echo signal as a measurement result of the observation target of the ultrasound transducer 21 from the ultrasound endoscope 2 (step S1).

The signal amplification unit 311 that receives the echo signal from the ultrasound transducer 21 amplifies the echo signal (step S2). Here, the signal amplification unit 311 performs amplification (STC correction) of the echo signal based on, for example, a relationship between the amplification factor and the reception depth illustrated in FIG. 2.

Subsequently, the B-mode image data generation unit 341 generates B-mode image data by using the echo signal amplified by the signal amplification unit 311 and outputs the B-mode image data to the display device 4 (step S3). The display device 4 that receives the B-mode image data displays a B-mode image corresponding to the B-mode image data (step S4).

The amplification correction unit 331 performs amplification correction on a signal outputted from the transmitting and receiving unit 31 so that the amplification factor is constant regardless of the reception depth (step S5). Here, the amplification correction unit 331 performs the amplification correction so that, for example, the relationship between the amplification factor and the reception depth illustrated in FIG. 3 is established.

Figure 9:
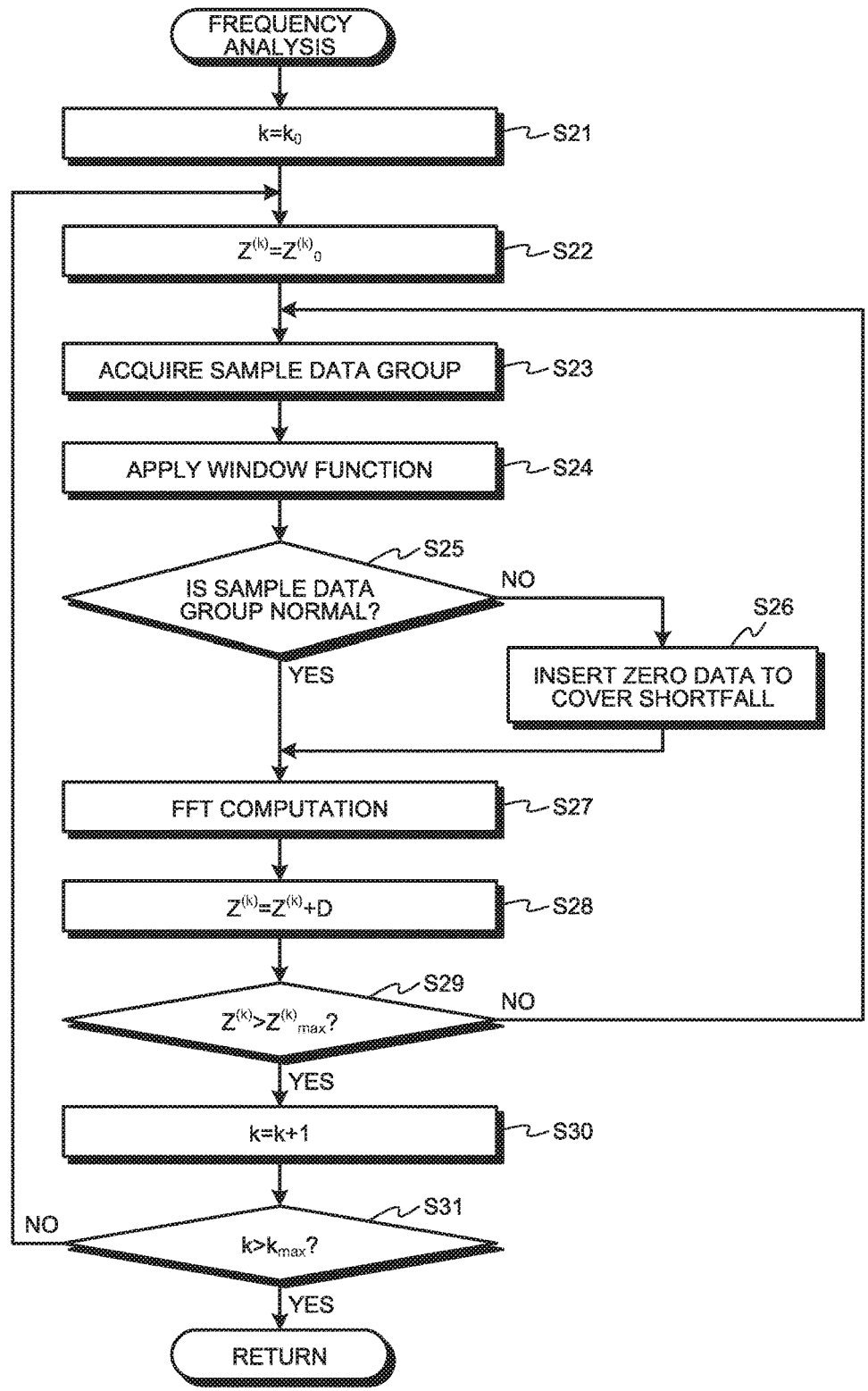
FIG. 9 is a flowchart illustrating an overview of processing performed by a frequency analysis unit of the ultrasound observation apparatus according to the embodiment of the present invention.

Thereafter, the frequency analysis unit 332 calculates frequency spectra for all the sample data groups by performing frequency analysis by FFT computation (step S6: frequency analysis step). FIG. 9 is a flowchart illustrating an overview of processing performed by the frequency analysis unit 332 in step S6. Hereinafter, the frequency analysis processing will be described in detail with reference to the flowchart illustrated in FIG. 9.

First, the frequency analysis unit 332 sets a counter k that identifies a sound ray of an object to be analyzed to $k_0$ (step S21).

Subsequently, the frequency analysis unit 332 sets an initial value $Z^{(k)}_0$ of a data position (corresponding to the reception depth) $Z^{(k)}$ that represents a series of data groups (sample data groups) to be acquired for the FFT computation (step S22). For example, as described above, FIG. 4 illustrates a case in which the eighth data position of the sound ray $SR_k$ is set as the initial value $Z^{(k)}_0$.

Thereafter, the frequency analysis unit 332 acquires a sample data group (step S23) and applies a window function stored in the storage unit 37 on the acquired sample data group (step S24). By applying the window function on the sample data group, it is possible to avoid the sample data group from being discontinuous at a boundary and prevent an artifact from being generated.

Subsequently, the frequency analysis unit 332 determines whether or not the sample data group at the data position $Z^{(k)}$ is a normal data group (step S25). As described when referring to FIG. 4, it is necessary that the sample data group has the number of data of power-of-two. Hereinafter, it is assumed that the number of data of a normal sample data group is $2^n$ (n is a positive integer). In the embodiment, the data position $Z^{(k)}$ is set to the center of the sample data group to which $Z^{(k)}$ belongs as much as possible. Specifically, since the number of data of the sample data group is $2^n$, $Z^{(k)}$ is set at a $2^n/2$th ($=2^{n-1}$th) position close to the center of the sample data group. In this case, a situation that the sample data group is normal means that there are $2^{n-1}$ ($=N$) data before the data position $Z^{(k)}$ and there are $2^{n-1}$ ($=M$) data after the data position $Z^{(k)}$. In the case illustrated in FIG. 4, the sample data groups $F_j$ (j=1, 2, . . . , and K−1) are all normal. FIG. 4 exemplifies a case in which n=4 (N=7 and M=8).

When the sample data group at the data position $Z^{(k)}$ is normal as a result of the determination of step S25 (step S25: Yes), the frequency analysis unit 332 proceeds to step S27 described later.

When the sample data group at the data position $Z^{(k)}$ is not normal as a result of the determination of step S25 (step S25: No), the frequency analysis unit 332 generates a normal sample data group by inserting zero data to cover the shortfall (step S26). A window function is applied to a sample data group that is determined to be not normal in step S25 (for example, the sample data group $F_K$ in FIG. 4) before zero data is added. Therefore, even if zero data is inserted in the sample data group, data discontinuity does not occur. After step S26, the frequency analysis unit 332 proceeds to step S27 described later.

In step S27, the frequency analysis unit 332 performs FFT computation by using the sample data group, so that the frequency analysis unit 332 obtains a frequency spectrum which is a frequency distribution of amplitude (step S27).

Subsequently, the frequency analysis unit 332 changes the data position $Z^{(k)}$ by a step width D (step S28). It is assumed that the step width D is stored in the storage unit 37 in advance. FIG. 4 exemplifies a case in which D=15. It is desirable that the step width D is coincident with a data step width that is used by the B-mode image data generation unit 341 when the B-mode image data generation unit 341 generates B-mode image data. However, when it is desired to reduce an amount of calculation performed by the frequency analysis unit 332, a value greater than the data step width may be set as the step width D.

Thereafter, the frequency analysis unit 332 determines whether or not the data position $Z^{(k)}$ is greater than a maximum value $Z^{(k)}_{max}$ in the sound ray $SR_k$ (step S29). When the data position $Z^{(k)}$ is greater than the maximum value $Z^{(k)}_{max}$ (step S29: Yes), the frequency analysis unit 332 increments the counter k by 1 (step S30). This means that the processing is transferred to an adjacent sound ray. On the other hand, when the data position $Z^{(k)}$ is equal to or smaller than the maximum value $Z^{(k)}_{max}$ (step S29: No), the frequency analysis unit 332 returns to step S23. By doing so, the frequency analysis unit 332 performs FFT computation on $[(Z^{(k)}_{max}-Z^{(k)}_0+1)/D+1]$ sample data groups for the sound ray $SR_k$. Here, [X] represents a maximum integer that does not exceed X.

After step S30, the frequency analysis unit 332 determines whether or not the counter k is greater than a maximum value $k_{max}$ (step S31). When the counter k is greater than $k_{max}$ (step S31: Yes), the frequency analysis unit 332 ends the series of frequency analysis processing steps. On the other hand, when the counter k is equal to or smaller than $k_{max}$ (step S31: No), the frequency analysis unit 332 returns to step S22. It is assumed that the maximum value $k_{max}$ is a value that is arbitrarily input by a user such as an operator through the input unit 35 or a value that is set in the storage unit 37 in advance.

In this way, the frequency analysis unit 332 performs FFT computation a plurality of times, on each of $(k_{max}-k_0+1)$ sound rays in an area to be analyzed. The results of the FFT computation are stored in the correction amount information storage unit 371 along with the reception depth and the receiving direction.

In the above description, the frequency analysis unit 332 performs the frequency analysis processing on all areas where the frequency analysis unit 332 receives the ultrasound signal. However, the frequency analysis unit 332 may perform the frequency analysis processing in only a set area of interest.

Following the frequency analysis processing in step S6 described above, the analysis data correction unit 333 calculates analysis data indicating a relationship between a signal value and a distance (reception depth) for each reception depth of a certain frequency based on a plurality of frequency spectra calculated by the frequency analysis unit 332 and corrects the analysis data based on a correction amount for each reception depth that is set in advance (step S7 to S9: analysis data correction steps).

In step S7, the analysis data correction unit 333 generates the analysis data indicating the relationship between the signal value and the distance (reception depth) for each reception depth of a certain frequency based on a plurality of frequency spectra calculated by the frequency analysis unit 332, for each frequency component.

In step S8, the analysis data correction unit 333 corrects the analysis data based on the correction amount for each reception depth that is set in advance. The analysis data correction unit 333 corrects the analysis data based on the correction amount (for example, differences $Q_1$ to $Q_7$ illustrated in FIG. 5) that is set for each reception depth.

In step S9, the analysis data correction unit 333 corrects the signal value of each reception depth and then generates a frequency spectrum as a frequency distribution of intensity at a certain reception depth z based on the analysis data after the correction. In other words, the analysis data correction unit 333 performs processing that restores the frequency spectrum described above based on the analysis data after the correction. The frequency spectrum $C_1$ illustrated in FIG. 6 is an example of the frequency spectrum obtained as a result of step S9.

Thereafter, the feature calculation unit 334 calculates each pre-correction feature of a plurality of frequency spectra corrected by the analysis data correction unit 333 and calculates a feature of each frequency spectrum by performing attenuation correction that eliminates effects of attenuation of ultrasound wave on the pre-correction feature of each frequency spectrum (steps S10 and S11: feature calculation steps).

In step S10, the approximation unit 334a calculates a pre-correction feature corresponding to each frequency spectrum by performing regression analysis on each of the plurality of frequency spectra generated by the analysis data correction unit 333 (step S10). Specifically, the approximation unit 334a approximates each frequency spectrum by a linear expression by performing regression analysis on each frequency spectrum and calculates the slope $a_0$, the intercept $b_0$, and the Mid-band fit $c_0$ as the pre-correction features. For example, the straight line $L_{10}$ illustrated in FIG. 7 is a regression line by which the approximation unit 334a approximates the frequency spectrum $C_1$ in the frequency band F by regression analysis.

Subsequently, the attenuation correction unit 334b performs attenuation correction on the pre-correction feature approximated by the approximation unit 334a with respect to each frequency spectrum by using the attenuation rate α and thereby calculates a correction feature, and stores the calculated correction feature into the storage unit 37 (step S11). The straight line $L_1$ illustrated in FIG. 7 is an example of a straight line obtained when the attenuation correction unit 334b performs the attenuation correction processing.

In step S11, the attenuation correction unit 334b calculates the correction feature by substituting a data position $Z=(f_{sp}/2v_s)Dn$ obtained by using data arrangement of a sound ray of an ultrasound signal into the reception depth z in the formulas (2) and (4) described above. Here, $f_{sp}$ is a data sampling frequency, $v_s$ is a sound speed, D is a data step width, and n is the number of data steps from a first data of the sound ray to a data position of a sample data group to be processed. For example, when the data sampling frequency $f_{sp}$ is 50 MHz, the sound speed $v_s$ is 1530 m/sec, and the data step width D is 15 by employing the data arrangement illustrated in FIG. 4, z=0.2295n (mm) is established.

The feature image data generation unit 342 generates the feature image data by superimposing the visual information (for example, color phase) associated with the feature calculated in step S11 on each pixel in the B-mode image data generated by the B-mode image data generation unit 341 (step S12: feature image data generation step).

Figure 10:
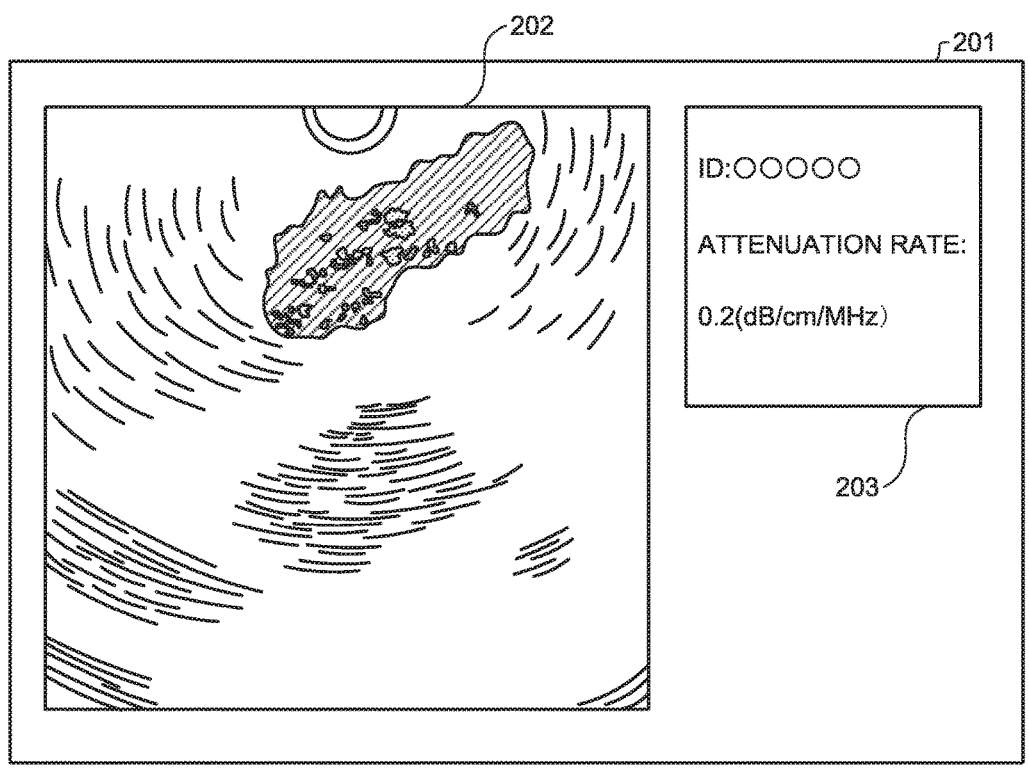
FIG. 10 is a diagram schematically illustrating a display example of a feature image of a display device of the ultrasound observation apparatus according to the embodiment of the present invention.

Thereafter, the display device 4 displays a feature image corresponding to the feature image data generated by the feature image data generation unit 342 under control of the control unit 36 (step S13). FIG. 10 is a diagram schematically illustrating a display example of the feature image in the display device 4. A feature image 201 illustrated in FIG. 10 includes a superimposed image display portion 202 that displays an image where the visual information related to the feature is superimposed on the B-mode image and an information display portion 203 that displays identification information of the observation target and the like. In the information display portion 203, information of the feature, information of approximation formula, image information such as gain and contrast, and the like may be further displayed. The B-mode image corresponding to the feature image may be displayed along with the feature image.

In a series of processing steps (steps S1 to S13) described above, the processing of step S2 and the processing of steps S4 to S11 may be performed in parallel.

According to the embodiment of the present invention described above, the analysis data correction unit 333 calculates the analysis data related to the signal value and the distance (the reception depth) for each reception depth of a certain frequency based on the frequency spectra calculated by the frequency analysis unit 332, corrects the analysis data based on the correction amount for each reception depth that is set in advance, and calculates the feature based on the corrected frequency spectrum, so that it is possible to uniformize the frequency spectrum in an analysis section and prevent the calculation accuracy of the frequency feature from being lowered even in a position other than the focus position.

In the embodiment, when the number of focus positions that can be set is only one, the analysis data is corrected based on a correction amount that is set for each frequency and determined according to a distance from the observation target.

In the description of the embodiment, an ultrasound wave is transmitted to an object for scattering the ultrasound wave uniformly or to a strong reflector such that a reference spectrum is obtained at a predetermined focus position and at a predetermined frequency, and the reference data is calculated based on the obtained signal data. However, a signal data at a predetermined frequency and a predetermined focus position may be obtained by using a receiver and the reference data may be calculated based on the obtained signal data. Examples of the receiver include a hydrophone that uses a piezoelectric element as a sensor.

While the embodiment of the present invention has been described, the present invention should not be limited to only the embodiment described above. For example, in the description, the correction value is set for each frequency component and for each focus position. However, a common correction value for each frequency component (a correction value independent of the focus position) may be used. It is possible to reduce the amount of data by using a common correction value for each frequency component (that is, the correction value is constant regardless of the focus position).

In the flowchart of FIG. 8 in the embodiment described above, the feature image data may be generated by using the frequency spectrum generated in step S9 without performing the attenuation correction shown in step S10 and step S11.

In the above-described embodiments, the frequency spectrum is calculated and corrected without specifying an area in particular. However, the frequency spectrum may be calculated and corrected only in an area of interest divided by specific depth width and sound ray width. In this case, the feature calculation unit 334 may individually set an optimal attenuation rate inside the set area of interest and outside the area of interest.

According to some embodiments, it is possible to prevent the calculation accuracy of the frequency feature from being lowered even in a position other than the focus position.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasound observation apparatus comprising:
   a processor comprising hardware, wherein the processor is configured to:
      perform a first amplification correction on echo signals of ultrasound echoes received by an ultrasound transducer, in which the greater a reception depth of an echo signal, the higher an amplification factor by which the echo signal is amplified to reduce an effect of attenuation that is distance dependent;
      generate digital radio frequency (RF) data based on the echo signals to which the first amplification correction has been performed;
      generate B-mode image data based on the digital RF data;

perform a second amplification correction on the digital RF data to offset an effect of the first amplification correction;
sample the digital RF data of sound rays of the ultrasound echoes on which the second amplification correction has been performed at predetermined time intervals to generate sample data;
perform Fast Fourier Transform (FFT) processing on sample data groups of the sample data, each of the sample data groups corresponding to one of a plurality of reception depths, to calculate a frequency distribution of intensity for each of the plurality of reception depths;
calculate a distance distribution indicating a relationship between intensity of a frequency spectrum and a distance for each reception depth of a certain frequency based on a plurality of frequency spectra;
acquire a correction amount for each reception depth that is set in advance,
wherein the correction amount is calculated from reference data,
wherein the reference data indicate a relationship between:
reception depths from the ultrasound transducer at a certain frequency and focus position; and
an intensity of the echo signal, and
wherein the correction amount for each reception depth is a difference between the reference data set for each reception depth and a correction value that is a constant value regardless of a distance;
correct the distance distribution based on the correction amount for each reception depth to reduce an effect of attenuation that is frequency dependent;
restore the frequency distribution based on the distance distribution that has been corrected based on the correction amount;
calculate a feature of the frequency distribution that has been restored; and
determine visual information based on the feature calculated.

2. The ultrasound observation apparatus according to claim 1,
wherein the processor is configured to:
control a display to display a visual image based on the visual information and a B-mode image based on B-mode image data.

3. A method comprising:
performing a first amplification correction on echo signals of ultrasound echoes received by an ultrasound transducer, in which the greater a reception depth of an echo signal, the higher an amplification factor by which the echo signal is amplified to reduce an effect of attenuation that is distance dependent;
generating digital radio frequency (RF) data based on the echo signals to which the first amplification correction has been performed;
generating B-mode image data based on the digital RF data;
performing a second amplification correction on the digital RF data to offset an effect of the first amplification correction;
sampling the digital RF data of sound rays of the ultrasound echoes on which the second amplification correction has been performed at predetermined time intervals to generate the sample data;
performing Fast Fourier Transform (FFT) processing on sample data groups of the sample data, each of the sample data groups corresponding to one of a plurality of reception depths, to calculate a frequency distribution of intensity for each of the plurality of reception depths;
calculating a distance distribution indicating a relationship between intensity of a frequency spectrum and a distance for each reception depth of a certain frequency based on a plurality of frequency spectra;
acquiring a correction amount for each reception depth that is set in advance,
wherein the correction amount is calculated from reference data,
wherein the reference data indicate a relationship between:
reception depths from the ultrasound transducer at a certain frequency and focus position; and
an intensity of the echo signal, and
wherein the correction amount for each reception depth is a difference between the reference data set for each reception depth and a correction value that is a constant value regardless of a distance;
correcting the distance distribution based on the correction amount for each reception depth to reduce an effect of attenuation that is frequency dependent;
restoring the frequency distribution based on the distance distribution that has been corrected based on the correction amount;
calculating a feature of the frequency distribution that has been restored; and
determining visual information based on the feature calculated.

4. The method according to claim 3, further comprising:
controlling a display to display a visual image based on the visual information and a B-mode image based on the B-mode image data.

5. A non-transitory computer-readable recording device storing instructions that cause a computer to at least:
perform a first amplification correction on echo signals of ultrasound echoes received by an ultrasound transducer, in which the greater a reception depth of an echo signal, the higher an amplification factor by which the echo signal is amplified to reduce an effect of attenuation that is distance dependent;
generate digital radio frequency (RF) data based on the echo signals to which the first amplification correction has been performed;
generate B-mode image data based on the digital RF data;
perform a second amplification correction on the digital RF data to offset an effect of the first amplification correction;
sample the digital RF data of sound rays of the ultrasound echoes on which the second amplification correction has been performed at predetermined time intervals to generate sample data;
perform Fast Fourier Transform (FFT) processing on sample data groups of the sample data, each of the sample data groups corresponding to one of a plurality of reception depths, to calculate a frequency distribution of intensity for each of the plurality of reception depths;
calculate a distance distribution indicating a relationship between intensity of a frequency spectrum and a distance for each reception depth of a certain frequency based on a plurality of frequency spectra;
acquire a correction amount for each reception depth that is set in advance, wherein the correction amount is calculated from reference data, wherein the reference data indicate a relationship between:
- reception depths from the ultrasound transducer at a certain frequency and focus position; and
- an intensity of the echo signal, and wherein the correction amount for each reception depth is a difference between the reference data set for each reception depth and a correction value that is a constant value regardless of a distance;

correct the distance distribution based on the correction amount for each reception depth to reduce an effect of attenuation that is frequency dependent;

restore the frequency distribution based on the distance distribution that has been corrected based on the correction amount;

calculate a feature of the frequency distribution that has been restored; and determine visual information based on the feature calculated.

6. The non-transitory computer-readable recording device according to claim 5, wherein the instructions further cause the computer to perform at least:

control a display to display a visual image based on the visual information and a B-mode image based on the B-mode image data.

* * * * *